United States Patent
Kowarz et al.

(10) Patent No.: US 11,877,866 B2
(45) Date of Patent: Jan. 23, 2024

(54) IMPLANTABLE APPARATUS FOR SENSING BIOLOGIC SIGNALS

(71) Applicant: EFFERENT LABS, INC., Buffalo, NY (US)

(72) Inventors: Marek Kowarz, Henrietta, NY (US); Spencer Rosero, Pittsford, NY (US)

(73) Assignee: EFFERENT LABS, INC., Buffalo, NY (US)

( * ) Notice: Subject to any disclaimer, the term of this patent is extended or adjusted under 35 U.S.C. 154(b) by 747 days.

(21) Appl. No.: 16/867,697

(22) Filed: May 6, 2020

(65) Prior Publication Data
US 2020/0352513 A1 Nov. 12, 2020

Related U.S. Application Data

(60) Provisional application No. 62/844,165, filed on May 7, 2019.

(51) Int. Cl.
  *A61B 5/00* (2006.01)
  *A61B 10/02* (2006.01)
  *G01N 21/64* (2006.01)

(52) U.S. Cl.
  CPC .......... *A61B 5/6865* (2013.01); *A61B 10/02* (2013.01); *G01N 21/64* (2013.01);
  (Continued)

(58) Field of Classification Search
  CPC .......... A61B 5/6865; A61B 10/02; A61B 2560/0219; A61B 2562/0233;
  (Continued)

(56) References Cited

U.S. PATENT DOCUMENTS 8,560,041 B2   10/2013   Flaherty et al.
9,225,190 B2   12/2015   Labbe et al.
(Continued)

FOREIGN PATENT DOCUMENTS

WO   2007012669 A1   2/2007
WO   WO-2007012669 A1 *  2/2007   ............. G01N 21/03

OTHER PUBLICATIONS

International Search Report and Written Opinion dated Jul. 31, 2020, PCT International Application No. PCT/US2020/031568, pp. 1-12.
(Continued)

*Primary Examiner* — Eric F Winakur
*Assistant Examiner* — Jonathan Drew Moroneso
(74) *Attorney, Agent, or Firm* — BioPharma Law Group, PLLC

(57) ABSTRACT

An implantable apparatus for physiological measurement in a host organism has an implantable sample chamber having a measurement port and live cells that are treated to fluoresce in response to light having an excitation wavelength. An optical sensor housing implanted within the host organism has a window to convey excitation light output and receive fluorescent light; a coupling that couples the measurement port of the sample chamber to the window; an optical chamber partitioned into an excitation sub-chamber and a detection sub-chamber, wherein both sub-chambers are in optical communication with the window; an excitation source energizable to direct excitation light through the excitation sub-chamber and to the window; and a detector in the path of fluorescent light received from the live cells. A signal processing apparatus is energizable to acquire and process a detector signal and to transmit a processed signal that is indicative of fluorescent light energy.

22 Claims, 13 Drawing Sheets

(52) U.S. Cl.
CPC .................. *A61B 2560/0219* (2013.01); *A61B 2562/0233* (2013.01); *G01N 2201/062* (2013.01); *G01N 2201/0693* (2013.01)

(58) Field of Classification Search
CPC ............ A61B 5/0031; A61B 2562/162; A61B 5/0071; A61B 5/076; G01N 21/64; G01N 2201/062; G01N 2201/0693; G01N 2201/0625; G01N 21/645
See application file for complete search history.

(56) References Cited

U.S. PATENT DOCUMENTS

| | | | |
|---|---|---|---|
| 9,808,187 B2 | 11/2017 | Freitag | |
| 2010/0202966 A1 | 8/2010 | Gross et al. | |
| 2012/0059232 A1* | 3/2012 | Gross ................. | A61B 5/14532 600/316 |
| 2012/0323094 A1* | 12/2012 | Palti ...................... | G01N 33/66 600/316 |
| 2015/0359472 A1* | 12/2015 | Botvinick ............ | A61B 5/1459 600/329 |
| 2016/0324449 A1* | 11/2016 | Gross .................. | A61B 5/1459 |
| 2018/0303387 A1 | 10/2018 | Dehennis et al. | |
| 2019/0113456 A1* | 4/2019 | Yamada ............. | G02B 21/0096 |

OTHER PUBLICATIONS

G. Wrigge et al., "Efficient coupling of photons to a single molecule and the observation of its resonance fluorescence", Nature Physics, vol. 4, No. 1, 2008, pp. 60-66.

* cited by examiner

IMPLANTABLE APPARATUS FOR SENSING BIOLOGIC SIGNALS

CROSS REFERENCE TO RELATED APPLICATIONS

Reference is made to, and priority is claimed from, commonly assigned U.S. Ser. No. 62/844,165, filed as a provisional patent application on May 7, 2019, entitled "IMPLANTABLE APPARATUS FOR SENSING BIOLOGIC SIGNALS" in the names of Marek Kowarz and Spencer Rosero, incorporated herein in its entirety.

FIELD OF THE INVENTION

The present invention is generally related to implantable sensors and, more particularly, to a device for facilitating measurement from living cells implanted within a host organism.

BACKGROUND OF THE INVENTION

Implantable medical devices play an increasing role in monitoring and treating disorders relating to numerous characteristics of a living organism. Implanted within a host organism, an implanted device can provide information that can be used to analyze, monitor and treat various disorders, including those of the circulatory system, the nervous system, the musculoskeletal system, and the gastrointestinal system, for example.

The utility and overall effectiveness of conventional sensing and monitoring elements is constrained by a number of factors, including risks and requirements for sensor placement, infection due to component or electrode insertion and removal, and other practical difficulties.

There appears to be considerable promise in the use of implantable sensing devices that employ living cells. Sensors using treated cells implanted within the host organism can provide highly accurate information on host conditions, based on physiologic responses associated with those cells. Among responses that can be particularly useful are fluorescence of particular types of treated cells in response to a stimulating source of light energy at suitable wavelengths.

However, the practical requirements of a sensing system for measuring cellular response can be daunting. In the face of challenges ranging from maintaining ongoing compatibility with the cell environment, to scaling device size for implantation, to distinguishing very faint signal content from high noise levels, to protecting sensitive instrumentation from fluids and other hazards, and meeting these challenges with as little disturbance to the host organism as possible, conventional approaches for signal acquisition and measurement are highly unsatisfactory in many cases.

Thus, while using implantable sensors in conjunction with a matrix or other living cell arrangement presents significant opportunities for measurement of physiologic conditions and response, numerous problems remain to be resolved. There is clearly a need for improved apparatus and methods that allow accurate measurement from living cells used for physiological sensing within implantable devices.

SUMMARY OF THE INVENTION

An object of the present disclosure is to advance the art of implantable device applications for measurement from living organisms.

According to one aspect of the present disclosure, there is provided an implantable apparatus for physiological measurement in a host organism, the apparatus comprising:

a) a sample chamber that is configured for implanting within the host organism, the sample chamber having a measurement port and live cells that are treated to fluoresce in response to light having an excitation wavelength, and wherein the sample chamber is configured to maintain fluid communication between the live cells and the host organism;

b) an optical sensor housing that is configured for implanting within the host organism, the optical sensor housing having:
   (i) a window disposed to convey excitation light output toward the sample chamber and to receive fluorescent light from the sample chamber;
   (ii) a coupling that couples the measurement port of the sample chamber in a fixed position relative to the window;
   (iii) an optical chamber that is partitioned into an excitation sub-chamber and a detection sub-chamber that is optically separated from the excitation sub-chamber, wherein both sub-chambers are in optical communication with the window;
   (iv) an excitation source that is energizable to direct light having the excitation wavelength along an excitation path through the excitation sub-chamber and to the window;
   (v) a detector that is disposed in the detection sub-chamber in a detection path of fluorescent light received from the live cells;
and c) a signal processing apparatus that is in signal communication with the detector and is energizable to acquire and process a detector signal and to transmit a processed signal that is indicative of fluorescent light energy.

These objects are given only by way of illustrative example, and such objects may be exemplary of one or more embodiments of the disclosure. Other desirable objectives and advantages inherently achieved by the disclosure may occur or become apparent to those skilled in the art. The invention is defined by the appended claims.

BRIEF DESCRIPTION OF THE DRAWINGS

The foregoing and other objects, features, and advantages of the disclosure will be apparent from the following more particular description of the embodiments of the disclosure, as illustrated in the accompanying drawings. The elements of the drawings are not necessarily to scale relative to each other.

DETAILED DESCRIPTION OF THE INVENTION

Figure 1:
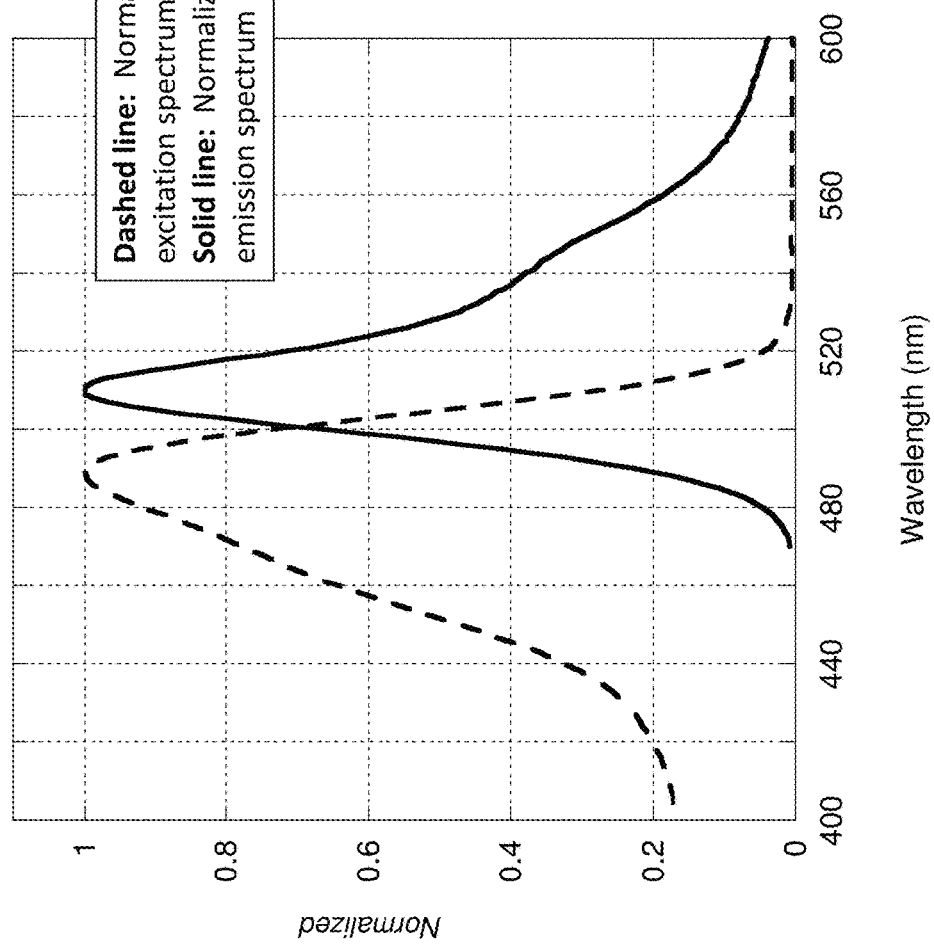
FIG. 1 is a graph showing Enhanced GFP (EGFP) excitation and emission spectra.

The following is a detailed description of the preferred embodiments of the disclosure, reference being made to the drawings in which the same reference numerals identify the same elements of structure in each of the several figures.

Where they are used, the terms "first", "second", and so on, do not necessarily denote any ordinal, sequential, or priority relation, but are simply used to more clearly distinguish one element or set of elements from another, unless specified otherwise.

In the context of the present disclosure, the term "coupled" is intended to indicate a mechanical association, connection, relation, or linking, between two or more components, such that the disposition of one component affects the spatial disposition of a component to which it is coupled. For mechanical coupling, two components need not be in direct contact, but can be linked through one or more intermediary components. Coupling can use various mechanisms, including one or more clips, suction cups, magnets, clamps, mechanical fittings, adherence by electrostatic forces, adhesion, hook and loop or fiber linkages such as those provided by VELCRO® Brand fasteners from Velcro Companies, or screws or other fasteners, including removable fasteners.

In the context of the present disclosure, the terms "optic" and "optics" are used generally to refer to lenses and other types of refractive, diffractive, or reflective components or apertures used for shaping, redirecting, and repositioning light.

In the context of the present disclosure, the term "host" or "host organism" refers to a living creature into which the implantable apparatus of the present disclosure is implanted.

The phrase "in signal communication" as used in the present application means that two or more devices and/or components are capable of communicating with each other via signals that travel over some type of signal path. Signal communication may be wired or wireless. The signals may be communication, power, data, or energy signals which may communicate information, power, and/or energy from a first device and/or component to a second device and/or component along a signal path between the first device and/or component and second device and/or component. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

As used herein, the term "energizable" relates to a device or set of components that perform an indicated function upon receiving power and, optionally, upon receiving an enabling signal.

The phrase "in optical communication" as used in the present application means that two or more devices and/or components are capable of passing light between them.

According to an embodiment of the present disclosure, as described in U.S. Pat. No. 8,024,020 entitled "System and Method for Stimulation of Biologic Signals in a Bio-Electro-Physiologic Matrix" to Rosero, cells of the host organism are treated to serve as sensors. For example, the cells of interest for an organ or system of the host, or other suitable source, can be biopsied, nurtured in a biocompatible support matrix, and restored into a position within the host. Alternatively, the living cells sustained within the host and used for sensing may come from a different cell "donor" of the same species as the host, or even from an altogether different species. The term "sustained" has its conventional meaning, essentially, being kept alive. For the purpose of sustaining sensor cells, there must be at least some fluid communication between the implanted sensor cells and the host organism. In addition, in order to sustain the living cells, there may need to be some barrier against protective mechanisms of the host, for example, a barrier against an immune response by the host.

The living cells may be modified or genetically engineered for specific function, such as by treatment using a detection protein. One exemplary protein that can be employed for use within living cells is green fluorescent protein (GFP), which can be extracted from jellyfish. This protein can be attached to a host protein and maintained within the living organism. GFP emits green light with a peak wavelength near 510 nanometers (nm) when it is excited with violet light with a wavelength near 400 nm. GFP fluorescence intensity varies according to the relative amount of GFP present in the cell. Alternatively, an intracellular dye may also be used instead of GFP.

As another example, Enhanced GFP (EGFP) has excitation and emission spectra in similar ranges, as shown in the graph of FIG. 1. Exemplary spectral characteristics for filters for the optical apparatus of the present disclosure are based on EGFP values. It can be appreciated that different filter sets can be used, appropriately matched to the characteristics of the fluorescing agent within sample cells, as described in more detail subsequently.

When the treated cell sample acts as a sensory device, even slight changes in the host condition can be sensed in the physiologic response. For measurement, the treated cell sample can be actively scanned and used to analyze the physiology of living biologic materials.

Although the capability for sensing biological conditions using genetically treated cells offers particular promise for obtaining valuable information relative to a host condition, there are considerable challenges for making this sensing practical, including the following:

(i) size and form factor of the sensing components. In order to be implantable within the host, the sensing components must be as small and streamlined as possible in design.

(ii) maintaining treated cells in a viable state. The treated sample must be sustained by the host, able to receive nutrient and remain alive within the host throughout the measurement period. The duration of the measurement period can be variable, and can even last several weeks, months or for longer term; in general, multiple measurements of sample response must be obtained over time.

(iii) extremely high sensitivity to noise. The ratio of excitation photons to the sensed photons is typically well above 100,000 (1.0E+5) to 1 and can be on the order of 1 million (1.0E+6) to 1 or even as large as 1 billion (1.0E+9) to 1. The detector signal is thus very near the noise level. Some type of noise filtering significantly improves the ability to distinguish the true signal from noise content.

(iv) limited dynamic range. Measurement of the low signal levels from the treated cells requires significant amplification. Any background signal unrelated to the treated cells is amplified as well, and can limit the dynamic range of the detector, even leading to detector saturation that prevents signal measurement.

(v) maintaining a stable positional relationship between sensing device optics and the treated sample. In each measurement cycle, sensing should acquire measurement data over the same region of the sample. Even slight changes in the positional or angular relationship between the sensor and the sample can change signal levels and compromise data quality.

(vi) protection of sensing components from body fluids. Fluid communication or fluid exchange can be maintained between the retained live sensor cells that serve as the physiological measurement elements or "sample" and the host organism. However, the bodily fluids must be prevented from obscuring the optical path used for sensing and from short-circuiting the electronic components used for signal conditioning and processing. Both the electronics and the signal emission/acquisition optics should be appropriately sealed and kept free from fluids.

(vii) communicating data from the implanted sensor. Wiring for power and signal content is feasible; however, wiring can be invasive and uncomfortable to the host or may even render the sensor unusable in some cases.

(viii) providing power to sensor and processing components. Some type of power source must be provided.

Embodiments of the present disclosure address challenges (i)-(viii) given above and provide a compact, sensitive, and efficient solution for measurement of signals from within the host metabolism.

Figure 2A:
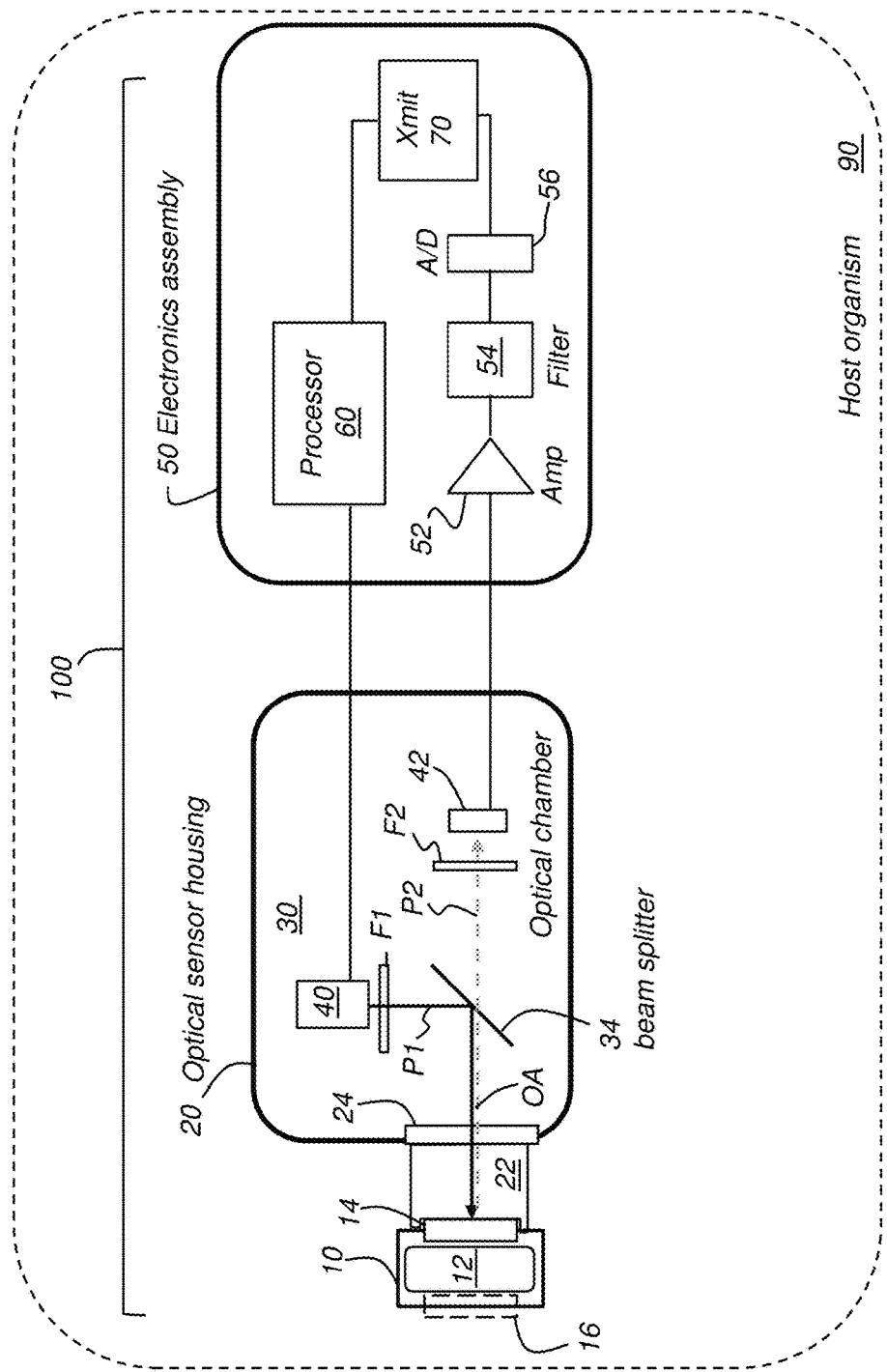
FIG. 2A is a schematic diagram that shows components of an implantable sensor apparatus according to an embodiment of the present disclosure.
Figure 2B:
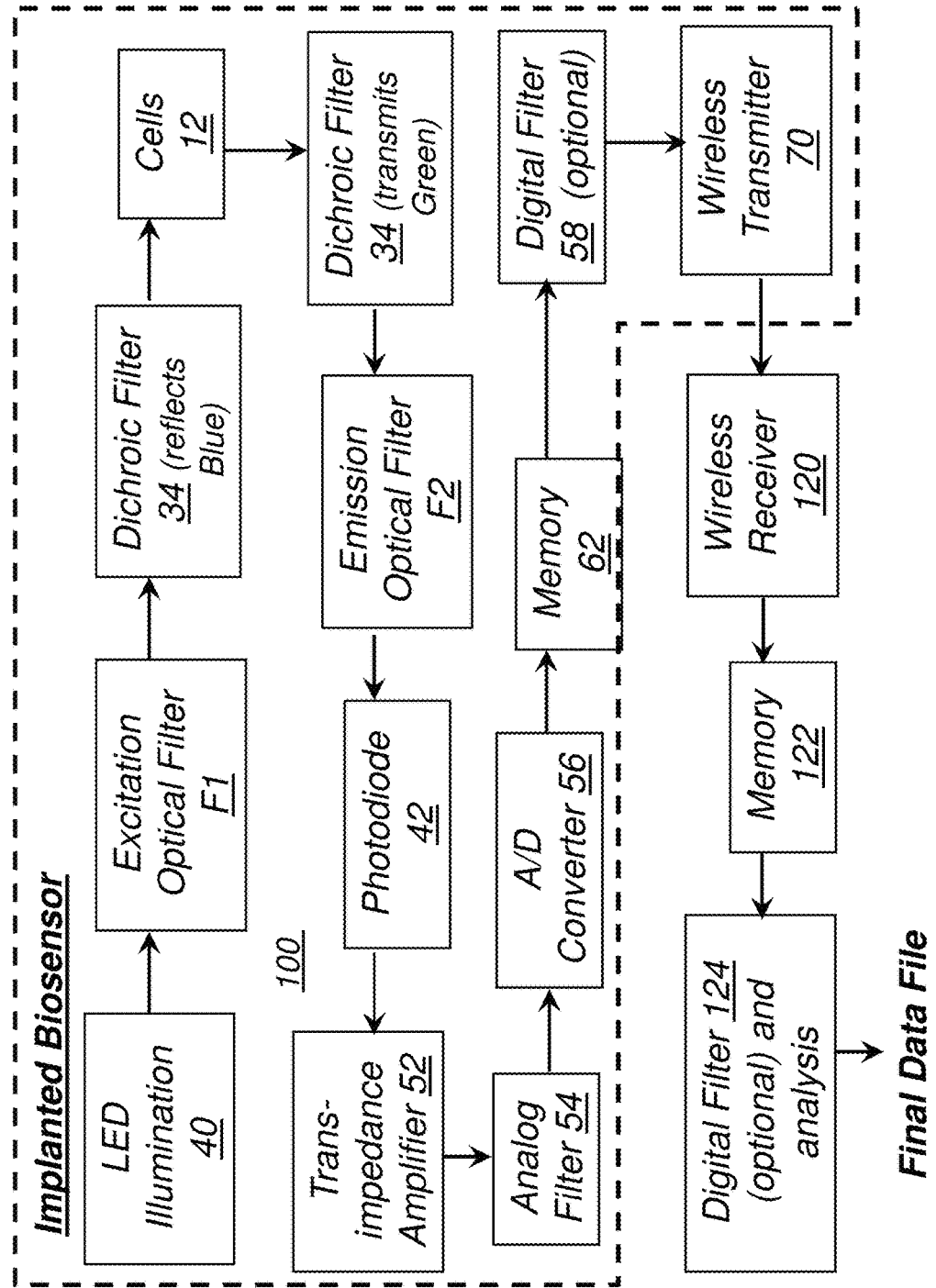
FIG. 2B is a signal flow diagram that shows components of the implantable sensor apparatus shown in FIG. 2A.

The schematic view of FIG. 2A and signal flow diagram of FIG. 2B show component functions and operation for an embodiment of the present disclosure having an implantable sensor apparatus 100 configured for monitoring physiological condition of treated cells 12 sustained in a host organism 90. A cell sample chamber 10 provides an implantable housing suitable for treated cells that serve as sensor cells 12. Sensor cells 12 are treated to fluoresce in response to an illumination signal of an excitation wavelength. The fluorescence that can be sensed along a detection path exhibits changes in intensity in response to physiological change within the host organism 90. An optical port 14 for measuring the fluorescence energy changes is formed along one surface of cell sample chamber 10. The optical port 14 may include a transparent glass or plastic window, commonly shared for conveying light energy on both illumination and detection optical paths. Ongoing fluid communication is maintained between sensor cells 12 and the host organism. An optional permeable membrane, shown in dashed line form as membrane 16 on another surface of chamber 10, can act as a microfluidic filter that provides a protective barrier between treated sensor cells 12 and other host organism cells, while at the same time allowing both continuous fluid communication or exchange and gas exchange to and from the host organism 90 in order to sustain cell 12 life. The treated sensor cells may reside on the interior surface of membrane 16, or on the interior surface of the (optional) transparent window, or in a suitable biocompatible matrix that is supported in position, such as between optical port 14 and membrane 16.

Cell sample chamber 10 is configured to be coupled to an optical sensor housing 20. A coupling 22 fixes the position of optical port 14 of cell chamber 10 to a measurement window 24 of an optical chamber 30, along an optical axis OA. Any of a number of types of mechanisms can be used as coupling 22, including spring-loaded clips; one or more magnets; screws or other fasteners; and biocompatible adhesives, including pressure-sensitive tape or suitable epoxies (light or chemically cured). In some embodiments, the coupling between cell chamber 10 and optical sensor housing 20 may include a gasket, an O-ring, or other mechanism for preventing fluid from entering the space between the optical port 14 and measurement window 24.

Continuing with FIGS. 2A and 2B, an electronics assembly 50 is in signal communication with components within an optical chamber 30 in optical sensor housing 20 and provides the needed control and signal conditioning logic for obtaining measurements from sensor cells 12. According to an embodiment of the present disclosure, electronics assembly 50 is packaged within optical sensor housing 20, such as formed on a circuit board that extends along a plane that is parallel to a plane defined by the primary optical paths for emitted fluorescent light and sensed light energy within optical chamber 30. This allows a single housing, implanted within the host organism 90, to enclose both the optics and the electronics needed for a wireless embodiment.

Alternately, functions of electronics assembly 50 could be provided by components external to host 90. For this alternate configuration, optical sensor housing 20 is implanted and connected by wires or other communication channel to external electronics for signal control and measurement.

The signal flow diagram of FIG. 2B shows the progression of optical and electrical signals through components of implantable sensor apparatus 100 and to external processing and storage components. An excitation optical filter F1 conditions emitted light from the solid-state excitation source 40. Filter F1 can be treated to attenuate unwanted excitation wavelengths from source 40, such as wavelengths from the excitation source that may be in the fluorescent emission signal range. Dichroic filter 34 is typically configured as a beam splitter, whose function is to separate excitation from fluorescence energy light paths, as described in more detail subsequently. The filtered light is directed to live sensor cells 12, which are treated to fluoresce when stimulated by excitation energy. For live sensor cells 12 that are treated with EGFP, the excitation light is typically in the blue range; the fluoresced sample signal light, at higher wavelengths, is typically in the green range.

Subsequent components in the signal flow sequence condition and transmit the measurement signal obtained from cell fluorescence. The fluoresced light signal from the sample sensor cells 12 is incident on the dichroic filter 34 beam splitter, which is conditioned to transmit the low-level fluoresced light, directed through emission filter F2, which is conditioned to attenuate and eliminate stray or scattered light outside of the fluorescent emission signal wavelength band. Emission filter F2 is particularly useful for blocking any residual excitation light. The filtered fluorescent signal is converted from photons to electrons by a photodiode 42 or other suitable optical detector that generates a signal current. A trans-impedance amplifier 52 amplifies and converts the current signal to a voltage signal. An analog filter 54 removes noise from the voltage signal and provides the signal to an A/D converter 56 for digitization. The digital data that is generated is buffered in some type of memory circuit 62 and may be filtered by a digital filter 58. Transmitter 70, which is shown as a wireless transmitter in the FIG. 2B embodiment, transmits the digital data out of the host organism to a wireless receiver 120. The received data is buffered or recorded in a memory 122 and, optionally, is processed through a digital filter 124 and analyzed in order to provide a data file for subsequent processing.

The process outlined with respect to FIG. 2B can be continuous if power is continuously delivered to components of sensor apparatus 100. If desired, the signal sequence shown in FIG. 2B can be executed in a time-varying fashion, for example, periodically or on demand, such as in response to wired or wireless instructions from outside the host organism. This time-varying approach can provide several advantages such as conserving battery power, limiting photobleaching of the live sensor cells, and improving signal quality (i.e. improving signal-to-noise ratio).

Optical Sensor Housing 20

Optical sensor housing 20 is sealed to protect optical components from contact with surrounding bodily fluid. As is shown more clearly in FIG. 3A, optical chamber 30 is partitioned into two optical sub-chambers 26 and 28 that are optically and spatially separated from each other to eliminate scattered excitation light or to reduce scattered excitation light so that its effect on the detected signal is negligible. This separation may be provided by a dichroic beam splitter 34, for example. Optical sub-chamber 26 houses an excitation source 40 that is energizable to generate illumination with light energy of an excitation wavelength for treated sensor cell 12 fluorescence. Excitation source 40 can be a light-emitting diode (LED) or other solid-state light source, such as a laser.

Optical sub-chamber 28 houses an optical detector 42. Optical detector 42 can be a photodiode or other type of single or multi-element light sensor. Because of the low intensity of the fluorescence signal, optical detector 42 preferably has low noise and low dark current. In an alternative embodiment (not shown), optical detector 42 is a CCD or CMOS image sensor. In yet another embodiment, optical detector 42 is a chip-scale photodiode.

Figure 3A:
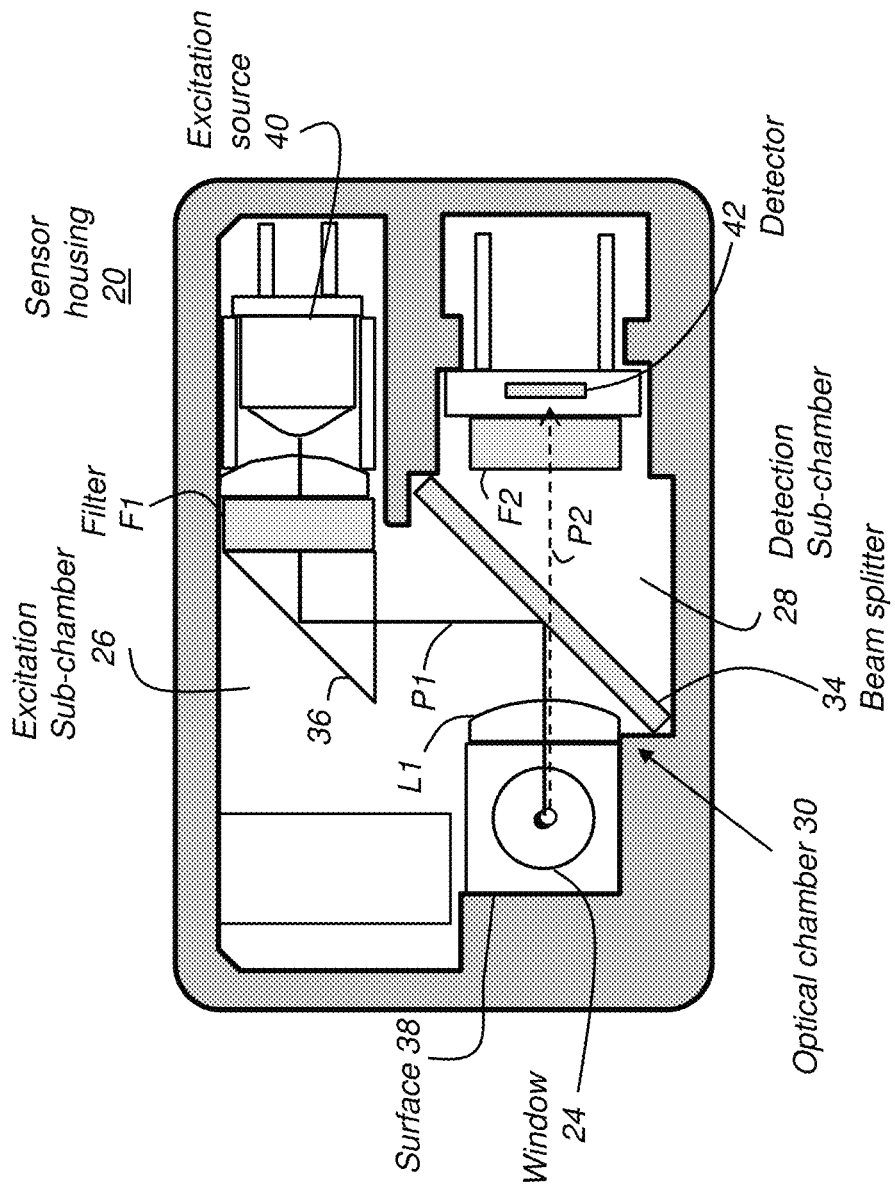
FIG. 3A is a top view showing an optical chamber partitioned into two optical sub-chambers that are optically and spatially separated from each other by a beam splitter.
Figure 3B:
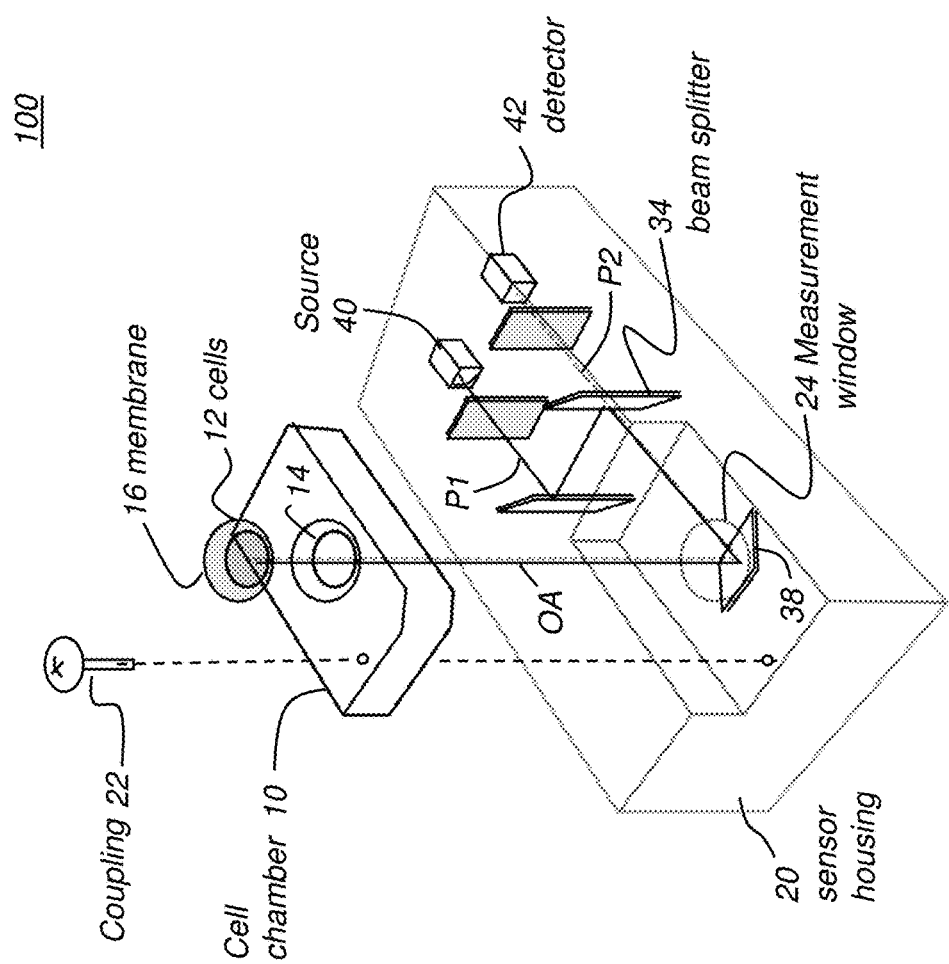
FIG. 3B is a schematic diagram in perspective view that shows, in exaggerated scale, the overall conceptual arrangement of the optical paths within an optical sensor housing and extending toward/returning from the sample.

FIG. 3B is a perspective view that shows, with exaggerated distance and partially exploded view, the arrangement of optical paths within optical sensor housing 20 and extending toward and back from cell chamber 10. The optical paths within a portion of optical chamber 30 are shared, with optical paths P1 and P2 both extending between a surface of beam splitter 34 and the sample, sensor cells 12 visible through window 24 and optical port 14, and with separate optical paths provided within optical chamber 30. Path P1 extends separately from path P2 in that section between the same surface of the beam splitter 34 and the excitation source 40. Detection path P2 is separate from path P1 between the opposing surface of beam splitter 34 and detector 42. FIGS. 3A and 3B show an excitation light path P1 along a bold, solid line, with signal light path or detection path P2 marked as a dashed line path that extends toward detector 42 in optical sub-chamber 28. System optics define a folded optical axis OA that extends between the sensor cells 12 of the sample and the detector 42.

Figure 3C:
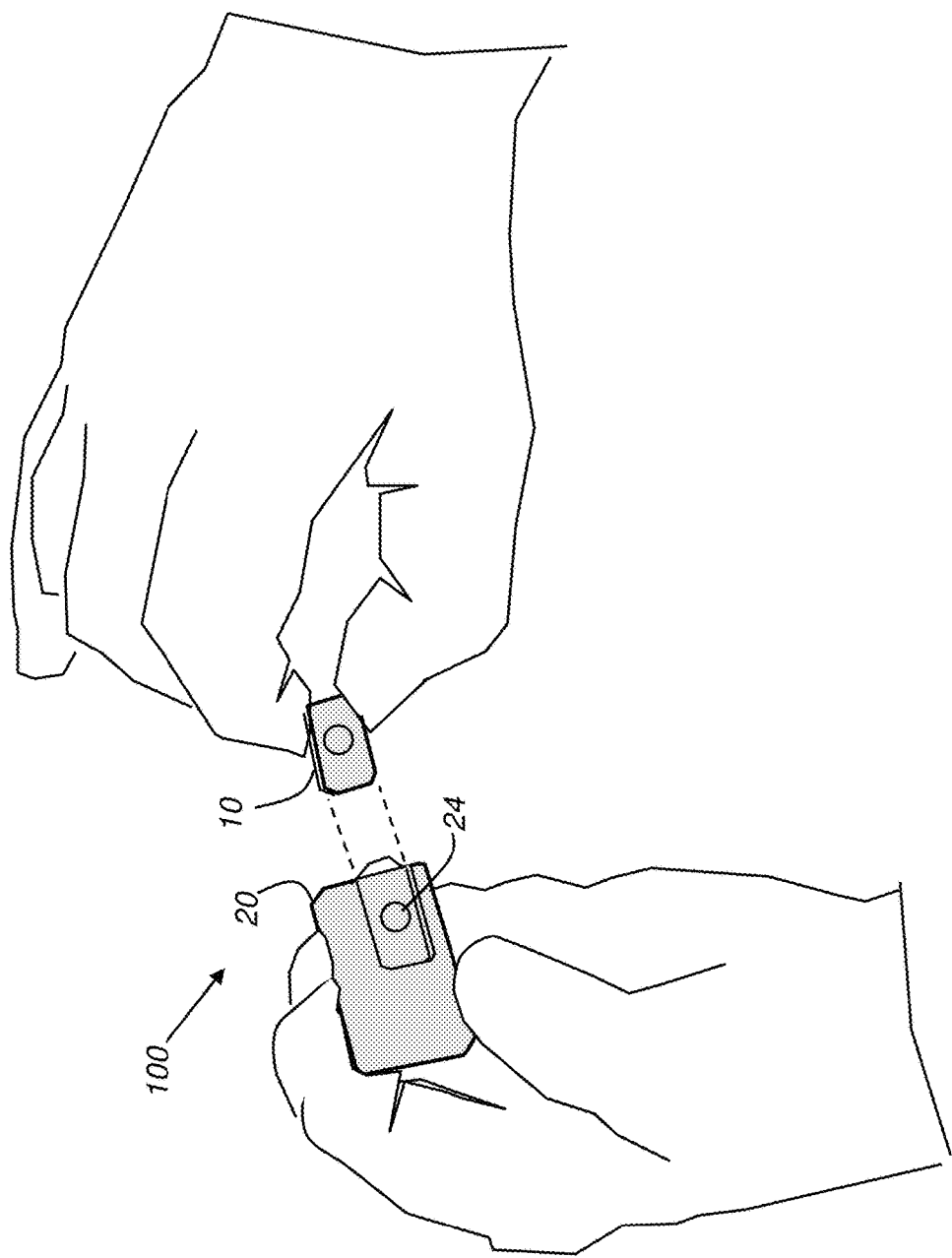
FIG. 3C is a perspective view that shows a cell chamber removed from its coupled position against an optical sensor housing.

FIG. 3C shows coupling/de-coupling of cell chamber 10 from window 24 on sensor housing 20. FIG. 3C also provides an idea of scale for an embodiment of the combined implantable sensor apparatus 100. Ideally, for implantation within a host organism, the sensor housing 20 can be made as small as possible with rounded contours to minimize any injury or physical discomfort to the host.

Figure 4:
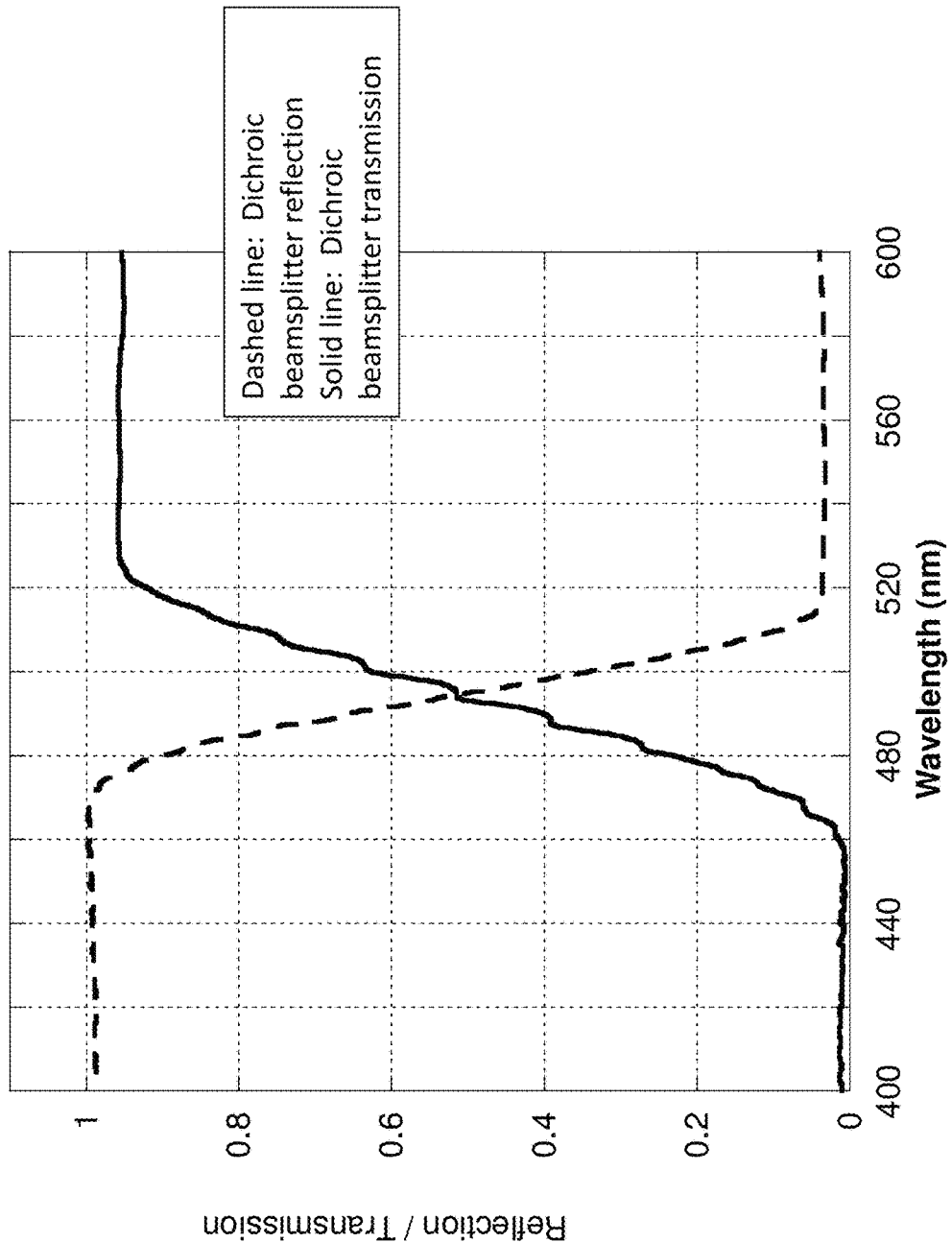
FIG. 4 is a graph that shows characteristic curves of transmission and reflection for an exemplary dichroic beam splitter.

Beam splitter 34 can be a dichroic beam splitter, configured to transmit green light and reflect blue light wavelengths. The graph of FIG. 4 shows characteristic curves for transmission and reflection for an exemplary dichroic beam splitter component used as beam splitter 34. There is high reflectance for blue wavelength illumination from excitation source 40 (nominally 420-495 nm) and high transmission for green wavelengths fluoresced from sensor cells 12 (nominally 495-570 nm).

Reflective surfaces 36 and 38 shown in FIGS. 3A and 3B can be used for redirecting the path of light within optical chamber 30. Right-angle prisms, mirrors, or other reflective surfaces can be used for this purpose. In the component and optical path orientation shown in FIG. 3A, the light paths for excitation illumination and emitted fluorescent signal light to and from beam splitter 34 lie within the same "primary" plane, parallel to the page surface. Reflective surface 38 can be a turning prism for directing light into or out of the primary plane. Window 24 directs light into or out of the page, as indicated in FIG. 3A by the solid and hollow dots superimposed within window 24.

Figure 5:
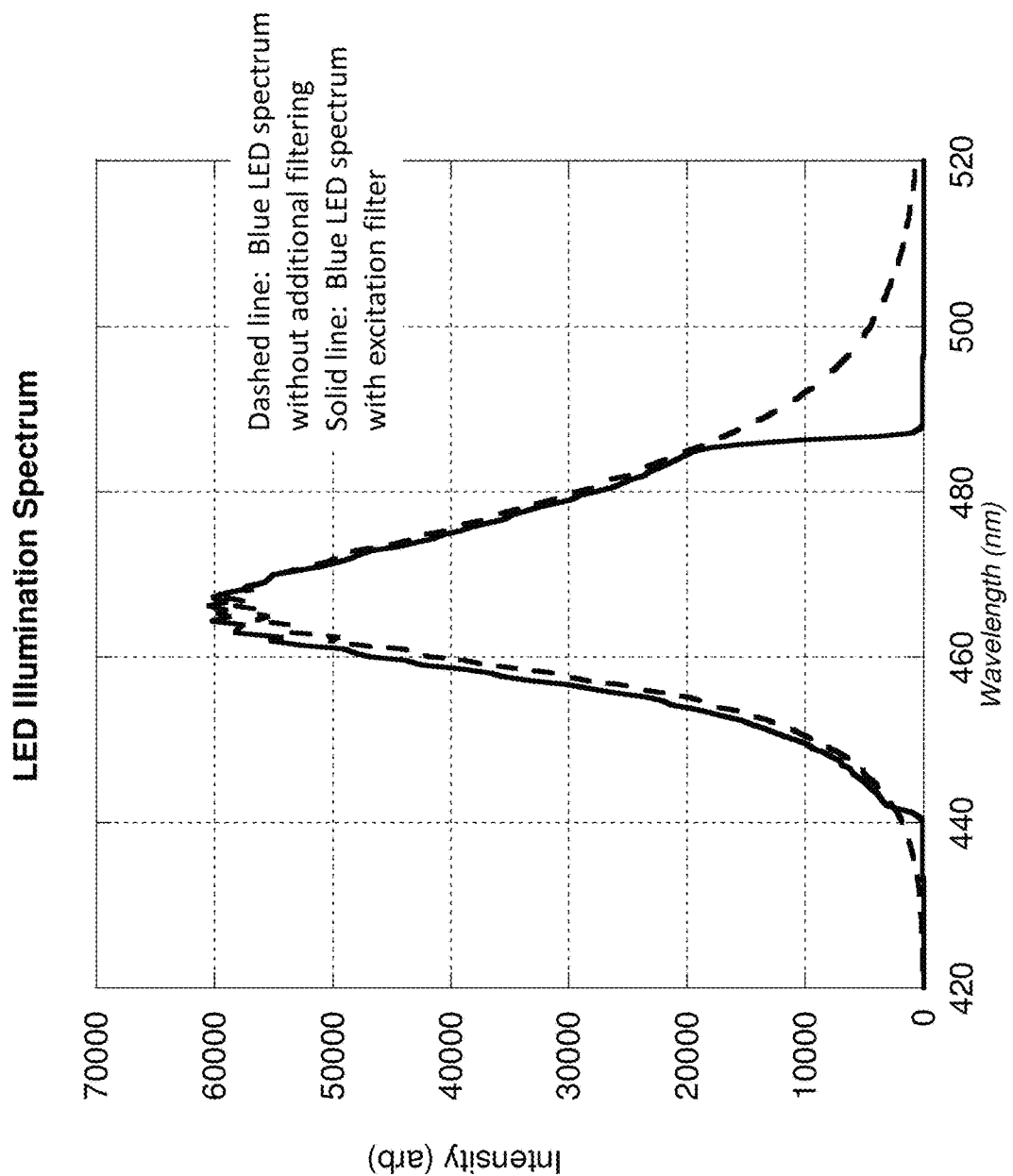
FIG. 5 is a graph that shows the results of filtering the excitation source with a suitable bandpass filter.

A number of additional optical components can be disposed along optical paths P1 and P2 for improving efficiency and performance of the optical system. One or more bandpass filters F1 within excitation sub-chamber 26 can help to attenuate excitation wavelengths outside the intended range for excitation. Particularly important is that bandpass filters F1 must block any wavelengths from the excitation source that extend into the fluorescent emission signal range. FIG. 5 shows the results of filtering the excitation source with a suitable bandpass filter F1.

Figure 6:
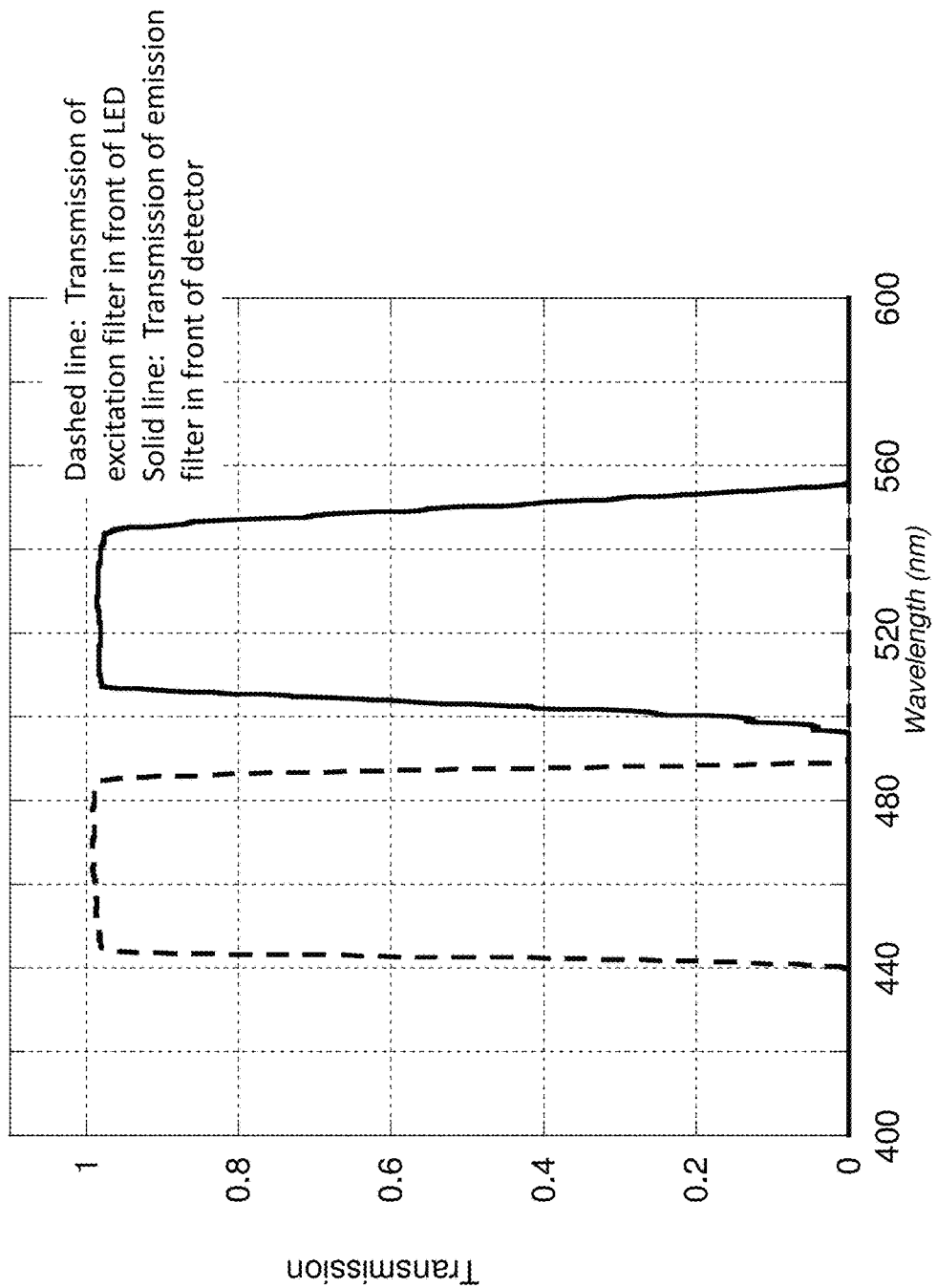
FIG. 6 is a graph that shows, for an embodiment of the present disclosure, the transmission characteristics for filters over a range of wavelengths.

Within detection sub-chamber 28, one or more band pass filters F2 help to block stray or scattered light outside of the fluorescent emission signal wavelength band. The graph of FIG. 6 shows, for an embodiment of the present disclosure, the transmission characteristics for filters F1 and F2 over a range of wavelengths. The FIG. 6 graph can be compared against the input excitation and output emission spectra for enhanced green fluorescent protein (EGFP), given in FIG. 1.

In addition, one or more lenses L1 can be provided along the appropriate optical path for improving light focus and other features.

Various features and components of optical chamber 30 serve to selectively combine and isolate the optical paths for excitation light energy and the sensed detection signal. As noted previously, the relative difference in energy level relates to the sizable difference in the ratio of excitation illumination photons to signal photons, a ratio in the range of about 1 million to 1 (1.0E+6:1) for relatively strong fluorescent signals to 1 billion to 1 (1.0E+8:1) for weak ones.

Particular design considerations for optical sensor housing components include the following:

(i) Reducing scattered light. Because the low-level sensed fluorescent light energy is difficult to discern from the high-level excitation light, embodiments of the present disclosure attempt to eliminate scattered excitation light from the light sensing path. A number of filters have been described; additional filters can be added in order to further attenuate light of unwanted wavelengths. Measures for reducing or eliminating scattered light include treatment of surfaces within sub-chambers 26 and 28, such as using light-absorbing paint or coatings or other known treatments for producing non-reflecting black surfaces. Particularly useful is treatment of surfaces in sub-chamber 28 so that any excitation light that unintentionally impinges on the surfaces within sub-chamber 28 is absorbed and not redirected towards detector 42.

Figure 8:
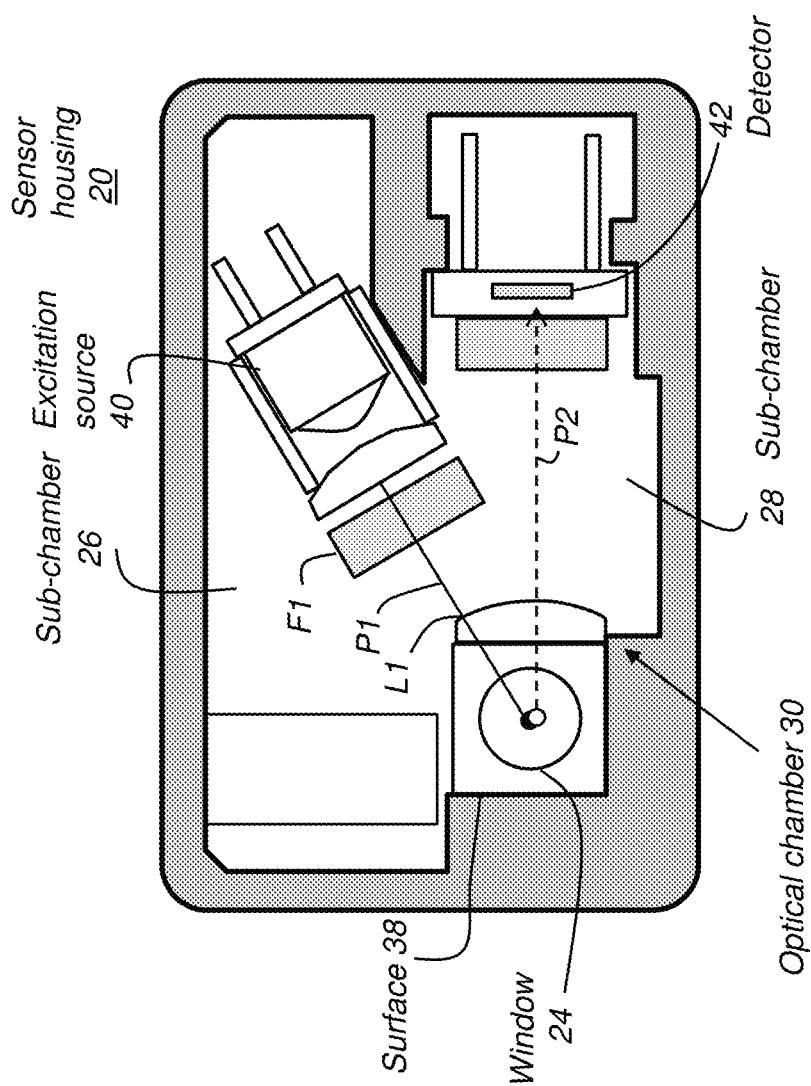
FIG. 8 is a schematic diagram that shows an embodiment of a sensor housing that employs angular separation of the excitation and fluorescent emission light paths.

(ii) Isolating optical sub-chambers from each other. This optical isolation consideration is corollary to the scattered light reduction of (i) given above. Particularly helpful is separation of fluorescent signal light from the excitation light, along with elimination of excitation light from detection sub-chamber 28. Optical isolation of detection sub-chamber 28 from excitation sub-chamber 26 can also be provided by beam splitter 34, which is shown in FIG. 3A extending fully across the opening between the two sub-chambers 26, 28. Beam splitter 34 and its associated support structure helps to eliminate light leakage and thus partitions optical chamber 30 into two optically separate, optically isolated sub-chambers. Angular separation of sub-chambers is another option, described subsequently with respect to FIG. 8.

(iii) Limited space is available for light-shaping and collecting optics.

Electronics Assembly 50

Continuing with FIGS. 2A and 2B, electronics assembly 50 includes a transimpedance amplifier 52 for converting detector current to voltage and increasing the signal strength of the relatively weak signal from detector 42. An optional electronic filter 54 helps to significantly reduce the noise content, which can be inadvertently enhanced by amplifier 52. An analog-to-digital (A/D) converter 56 then converts the amplified sensed signal to a digital value. An optional digital filter 58 can provide further filtering of the digital signal. An on-board memory 62 stores measured data for transmission. A control logic processor 60 provides control of excitation source 40 in optical chamber 30 and controls the data acquisition sequence for obtaining signal data from detector 42.

For a wireless sensor apparatus 100, a transmitter 70 is in signal communication with processor 60 and is energizable to transmit measured data that has been processed by electronics assembly 50. The transmitted data can be received by an external processor (not shown) such as a computer that can store, process, and display the measured data, for example. Transmission can use a standard radio frequency (RF) wireless protocol, such as Bluetooth protocol (based on IEEE standard 802.15.1), accessible to a wide range of handheld communications devices as well as to a range of desktop and instrumentation systems. Alternately, other wireless mechanisms can be used, including ultrasound.

At the receiving end, as described previously with reference to FIG. 2B, wireless receiver 120 acquires the transmitted signal and directs the digital content to memory 122. This signal data can be processed through optional digital filter 124 in order to provide the final data file.

Illustrative Example Values

By way of example, and not of limitation, some typical values for measurement using implantable sensor apparatus 100 that show the scale of measurement values under consideration are as follows:

Excitation peak wavelength: 465 nm
Excitation FWHM: 22 nm
LED current (typical): 30 mA
Output power output (typical) from window: 4.4 mW
Excitation photons per second from window (calculated): 1.03E+16
Emission band center wavelength for fluorescence: 531 nm
Fluorescence emission bandwidth: 46 nm
Transimpedance gain: 1.00E+08 (V/A)
Detector sensitivity: 0.28 (A/W)
Signal with background removed (typical): 110 mV
Signal optical power (calculated): 3.93 nW
Fluorescent signal photons per second (calculated): 1.05E+10

This example is for sensor cells that have enhanced green fluorescent protein (EGFP) and that have been biochemically stimulated to fluoresce. In this example, there is a very large difference (ratio of 1,000,000 to 1) between excitation photons and measured fluorescent signal photons, even when the cells fluoresce strongly.

Because of the low level of fluorescent signal photons, it is advantageous to reduce any residual ambient light, such as light from a nearby lamp or window for example, that penetrates into the host. This can be accomplished by orienting the optical sensor housing and sample chamber so that the housing also serves as a light shield to block ambient light from the sample chamber and from the illumination and sample light paths. In this configuration, the housing is disposed toward the skin of the host with the sample chamber underneath.

In practice, measurements are typically acquired at intervals. For example, measurements can be acquired every 20 minutes. However, measurements can be continuously obtained or taken on command. For embodiments where the sensor is fully implanted, wireless, and operates on battery power, the measurement interval should take finite battery life into account. For such wireless embodiments, transmitted sensor data also consumes battery power; this additional requirement must be accounted for in the measurement power budget.

Sensor Power

According to an embodiment of the present disclosure, battery power can be provided for operation. Batteries such as lithium ion or lithium polymer (LiPo) can be used. Radio frequency power can be employed wherein an antenna or coil on the sensor captures an RF signal provided by an external transmitter and the captured RF power is converted to suitable power for wireless sensor circuitry. Magnetic induction charging or magnetic resonance charging operate on similar principles to provide wireless energy. A charger source similar to that used in wireless charging for conventional cell phones can be used to effect wireless energy transfer and to charge rechargeable battery or other components. For power acquisition and delivery, a flexible patch or other charge-receiving surface or component can be attached to or implanted within the host organism.

For the case where some or most of the electronics assembly is external to the host and is connected by wire to the implanted optical sensor housing, DC power can be provided by a wired connection.

Electronic Signal Filtering

Figure 7A:
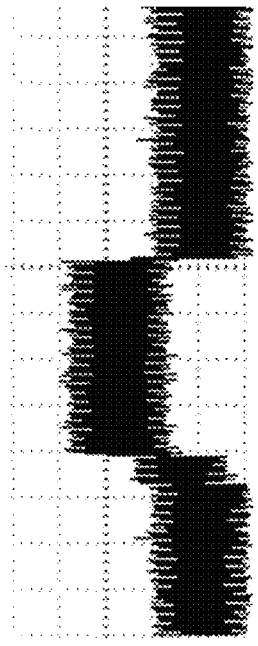
FIG. 7A is a graph that shows a typical, unfiltered signal typical for a non-fluorescing cell sample, pulsed with excitation light.
Figure 7B:
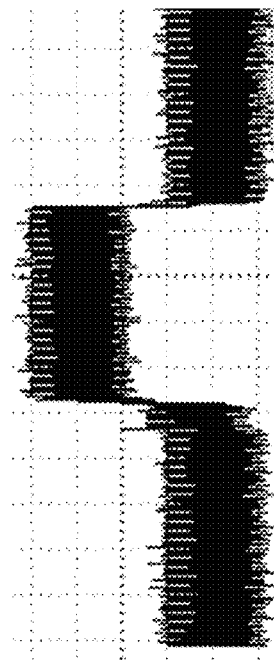
FIG. 7B is a graph that shows an unfiltered signal typical for a cell sample that has been treated to fluoresce.
Figure 7C:
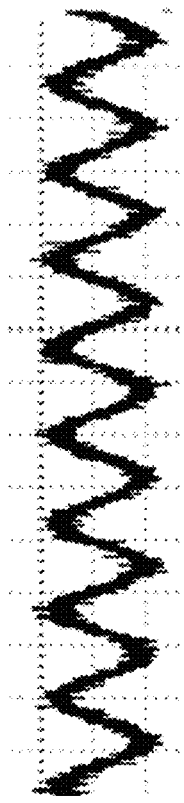
FIG. 7C is a graph that shows amplified noise from the 60 Hz indoor ambient, as well as amplified pickup of higher frequency sources of noise.

One problem inherent to implantation within a live host is a high level of background signal and noise. FIG. 7A shows an exemplary unfiltered signal typical for a non-fluorescing cell sample, pulsed with excitation light for about one second. By comparison, FIG. 7B shows an unfiltered signal typical for a cell sample that has been treated to fluoresce. FIG. 7C is a small interval (0.13 sec) of FIG. 7A that shows amplified noise from the 60 Hz indoor ambient, as well as amplified pickup of higher frequency sources of ambient noise. As FIGS. 7A-7C suggest, background signal and noise can have significant impact on the ability to obtain sensitive measurements in the implantation environment.

A variety of approaches can be implemented in order to improve measurement accuracy in the presence of the background and noise signal. For example, a combination of low-pass filtering and averaging can be used to measure the signal in FIGS. 7A and 7B to within a few tenths of a millivolt.

Varying illumination intensity over time can also help to reduce noise levels in the resulting output signal. For example, several short fluorescence measurements can be performed and the results averaged to improve the signal to noise ratio. Alternative methods can include modulation of the illumination source at a fixed frequency, such as at 1 kHz, and using a bandpass electronic filter to measure the amplitude of the fixed-frequency fluorescent signal that is emitted.

Figure 9A:
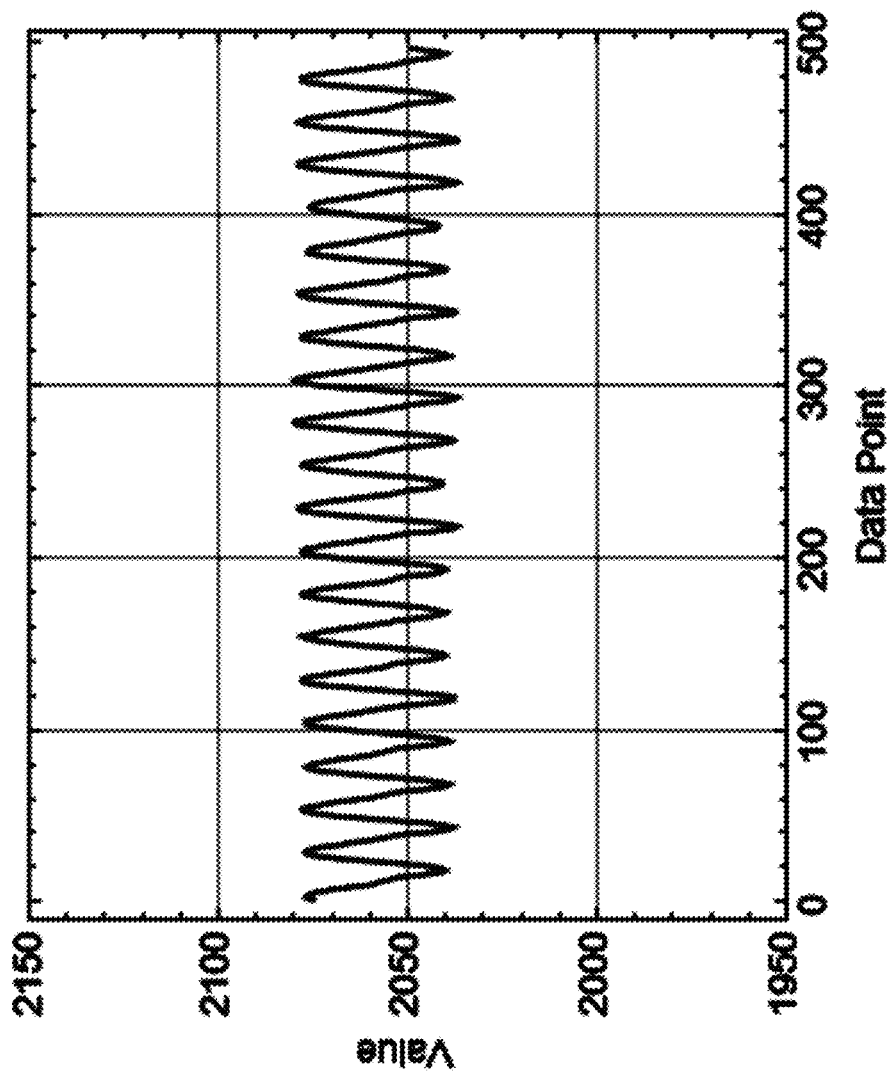
FIG. 9A shows a filtered output signal provided when applying sinusoidal modulation of illumination for a non-fluorescing cell sample.
Figure 9B:
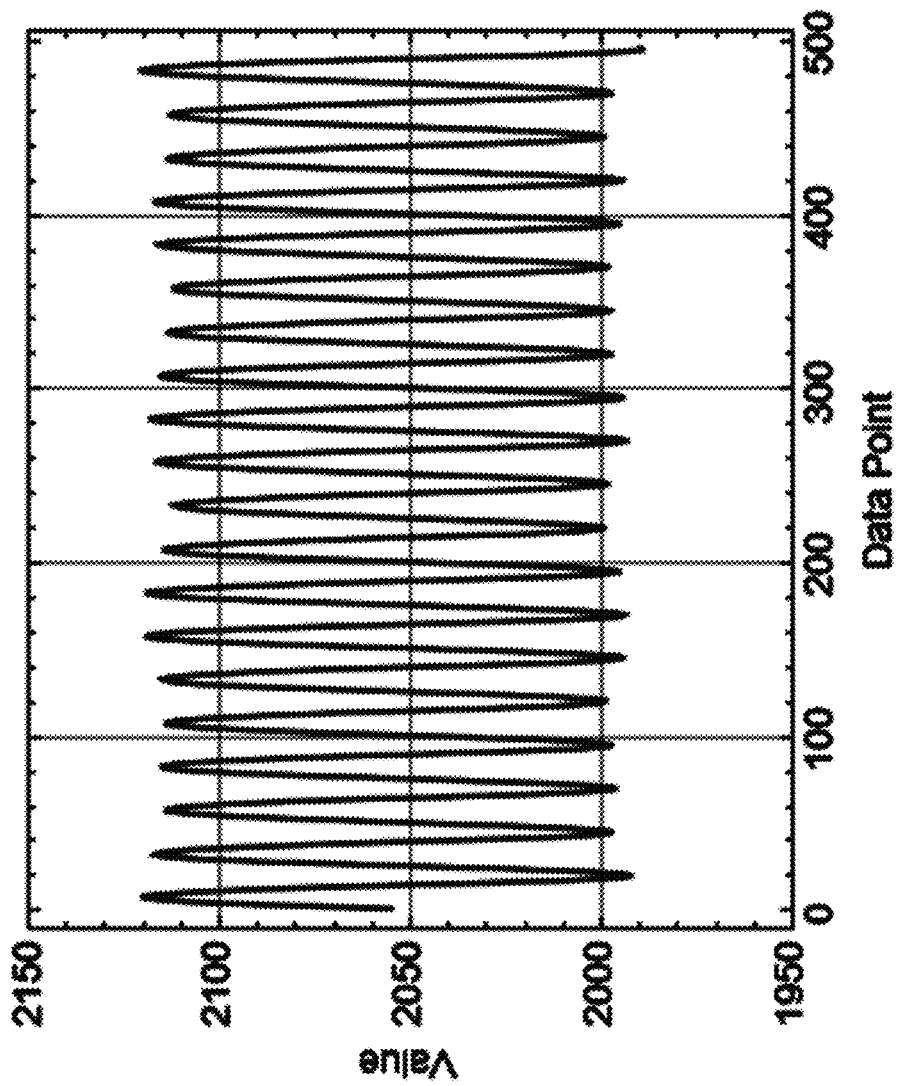
FIG. 9B shows a filtered output signal provided when applying sinusoidal modulation of illumination for a fluorescing cell sample.

FIGS. 9A and 9B show the results of applying sinusoidal modulation to the illumination from excitation source 40 and using bandpass filtering. For the example shown, source 40 is an LED driven by a current that is modulated to obtain the desired time-varying light output. FIG. 9A shows the output signal for non-fluorescent cells. FIG. 9B shows typical output for fluorescing cells using source modulation.

Strategies for Optical Separation

As noted previously, optical separation in sensor housing 20 between the input excitation light and the output emitted fluorescent light helps to eliminate or at least minimize the effects of scatter and reflection of excitation light towards optical detector 42. Additional approaches can supplement or replace the function of dichroic beam splitter 34 for providing the desired optical separation.

According to an alternative embodiment, the dichroic beam splitter 34 of FIGS. 3A and 3B is replaced by a polarization beam splitter (PBS), disposed at the same position. The polarization beam splitter reflects light having linear polarization along one axis and transmits light having linear polarization along the perpendicular axis. In this embodiment, excitation source 40 provides linearly polarized excitation light along excitation light path P1. Excitation source 40 can be, for example, a LED with a linear polarizer or a laser that emits linearly polarized light. The linearly polarized excitation light is reflected by the polarization beam splitter towards cell chamber 10 and excites the sensor cells. Fluorescent light energy from the sensor cells is unpolarized, containing light with both polarization axes. Along fluorescent signal light path P2, the polarization beam splitter transmits fluorescent light that is polarized perpendicular to the excitation light polarization. The perpendicularly polarized fluoresced light is then measured by optical detector 42. The polarization beam splitter redirects, away from optical detector 42, both excitation light reflected by cell chamber 10 as well as that portion of fluoresced light that is polarized parallel to the excitation light.

The polarization beam splitter may be used in conjunction with filters F1 and F2, as well as dichroic beam splitter 34. An additional linear polarizer may also be placed in front of optical detector 42 to further block misdirected excitation light.

As noted earlier, angular separation of the light paths is another possible alternative. Referring to the schematic diagram of FIG. 8, there is shown an embodiment of sensor housing 20 that employs angular separation of the excitation and fluorescent emission light paths. In this embodiment, reflections of excitation light by the cell chamber or from other components are displaced from optical detector 42 as a result of the angular separation. Fluorescent emission that emerges from cell chamber 10, which has no preferential angular orientation, is measured directly by optical detector 42.

There is described an implantable apparatus for physiological measurement in a host organism, the apparatus comprising a) a sample chamber that is configured for implanting within the host organism, the chamber having a measurement port and live cells treated to fluoresce in response to light having an excitation wavelength; an optical sensor housing that is configured for implanting within the host organism, the optical sensor housing having: (i) a window disposed to convey excitation light output and receive fluorescent light from the live cells in the sample chamber; (ii) a coupling that couples the measurement port of the sample chamber in a fixed position relative to the window; (iii) an optical chamber that is partitioned into an excitation sub-chamber and a detection sub-chamber that is optically separated from the excitation sub-chamber, wherein both sub-chambers are in optical communication with the window; (iv) an excitation source that is energizable to direct light having the excitation wavelength along an excitation path through the excitation sub-chamber and to the window; (v) a detector that is disposed in the detection sub-chamber in a sensor path of fluorescent light from the live cells; and c) a signal processing apparatus that is in signal communication with the detector and is energizable to acquire and process a detector signal and to transmit a signal that is indicative of the fluorescent light.

The measurement port can include a transparent window. The optical sensor housing can be sealed from fluid intake and implanted within the host organism. The optical chamber can be partitioned by a beam splitter. The signal processing apparatus can be within the optical sensor housing. The signal processing apparatus can be energizable to transmit a wireless signal. The coupling can be a magnetic coupling, a fastener, a clip, an adhesive tape, or an adhesive, for example. The excitation source can be a light-emitting diode. The detector can be a photodiode. The sensor sub-chamber can have one or more surfaces treated to absorb scattered light. There can be one or more optical filters along one or both the sensor path and the excitation path. The signal processing apparatus can be further configured to receive one or more encoded instruction signals. The apparatus can have a battery.

An implantable apparatus for reporting a physiological measurement from within a host organism can include an optical sensor housing that is configured for implanting within the host organism and that has a window and is energizable to generate an excitation light having an excitation wavelength, wherein the optical sensor housing is further configured to measure an emitted light from a sample, the emitted light having a fluorescent wavelength that is different from the excitation wavelength, wherein a ratio of excitation light photons to detected emitted light photons exceeds 100,000 to 1, and wherein the optical sensor housing is further configured to transmit a wireless signal indicative of the measured emitted light. A sample chamber can be configured for implanting within the host organism, the chamber having a measurement port and live cells, wherein the live cells are treated to fluoresce in response to the light having the excitation wavelength. A coupling can couple the measurement port of the sample chamber in a fixed position relative to the window of the optical sensor housing.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. An implantable apparatus for physiological measurement in a host organism, the apparatus comprising:
    a) a sample chamber that is configured for implanting within the host organism, the sample chamber having a measurement port and live cells that are treated to fluoresce in response to light having an excitation wavelength, and wherein the sample chamber is configured to maintain fluid communication between the live cells and the host organism;
    b) an optical sensor housing that is configured for implanting within the host organism, and which is configured to block ambient light from penetrating into the sample chamber, the optical sensor housing having:
        (i) a window disposed to convey excitation light output toward the sample chamber and to receive fluorescent light from the sample chamber;
        (ii) a coupling that couples the measurement port of the sample chamber in a fixed position relative to the window;
        (iii) an optical chamber that is partitioned by a beam splitter into an excitation sub-chamber and a detection sub-chamber, wherein the excitation sub-chamber and the detection sub-chamber are optically and spatially separated by the beam splitter, and wherein both sub-chambers are in optical communication with the window;
        (iv) an excitation source that is energizable to direct light having the excitation wavelength along an excitation path through the excitation sub-chamber and to the window;
        (v) a detector that is disposed in the detection sub-chamber in a detection path of fluorescent light received from the live cells; and
        (vi) a reflective surface disposed between the beam splitter and the sample chamber, wherein the reflective surface directs light into and out of a primary plane such that the excitation path and the detection path define a folded optical axis that extends between the live cells in the sample chamber and the detector; and
    c) a signal processing apparatus that is in signal communication with the detector and is energizable to acquire and process a detector signal and to transmit a processed signal that is indicative of fluorescent light energy.

2. The apparatus of claim 1 wherein the sample chamber further comprises a permeable membrane for continuously maintaining fluid communication.

3. The apparatus of claim 1 wherein the measurement port includes a transparent window.

4. The apparatus of claim 1 wherein the optical sensor housing is sealed from fluid intake.

5. The apparatus of claim 1 wherein the signal processing apparatus is within the optical sensor housing.

6. The apparatus of claim 1 wherein the signal processing apparatus is energizable to transmit a wireless signal.

7. The apparatus of claim 1 wherein the coupling is selected from the group consisting of a magnetic coupling, a fastener, a clip, an adhesive tape, and an adhesive.

8. The apparatus of claim 1 wherein the excitation source is a light-emitting diode.

9. The apparatus of claim 1 wherein the detector is a photodiode.

10. The apparatus of claim 1 wherein the detection sub-chamber has one or more surfaces treated to absorb scattered light.

11. The apparatus of claim 1 further comprising one or more optical filters along one or both the detection path and the excitation path.

12. The apparatus of claim 1 wherein the signal processing apparatus is further configured to receive one or more encoded instruction signals.

13. The apparatus of claim 1 further comprising a battery.

14. The apparatus of claim 13 wherein the battery is rechargeable using wireless energy transfer.

15. The apparatus of claim 1, wherein the coupling of the optical sensor housing in subpart (b)(ii), comprises a gasket or an O-ring for preventing fluid from entering the space between the optical port and the window.

16. An implantable apparatus for reporting a physiological measurement from within a host organism, the apparatus comprising:
    a) a sample chamber that is configured for implanting within the host organism, the sample chamber having a measurement port and live cells, wherein the live cells are treated to fluoresce in response to illumination having an excitation wavelength and an illumination intensity;
    b) an optical sensor housing that is configured for implanting within the host organism and that has a window and an optical chamber that is partitioned by a beam splitter into an excitation sub-chamber and a detection sub-chamber, wherein the excitation sub-chamber and the detection sub-chamber are optically and spatially separated by the beam splitter, and wherein both sub-chambers are in optical communication with the window, and wherein the optical sensor housing is energizable to generate the illumination, wherein the optical sensor housing is further configured to measure an emitted light from a sample, the emitted light having a fluorescent wavelength that is different from the excitation wavelength,
    wherein a ratio of excitation illumination photons to detected emitted light photons exceeds 100,000 to 1,
    wherein the optical sensor housing is further configured to transmit a wireless signal indicative of the measured emitted light;
    and c) a coupling that couples the measurement port of the sample chamber in a fixed position relative to the window of the optical sensor housing.

17. The apparatus of claim 16 wherein the sample chamber further comprises a permeable membrane for retaining the cells and maintaining fluid communication with the host organism.

18. A method for acquiring a physiological measurement from within a host organism, the method comprising:
   a) maintaining fluid communication between the host organism and live cells that are sustained within a sample chamber that is implanted within the host organism, wherein the live cells are treated to fluoresce in response to an excitation light energy having an excitation wavelength and an illumination intensity;
   b) within the host organism, directing the excitation light energy along a light path comprising a reflective surface that directs light out of a primary plane such that the light path defines a folded optical axis that extends into the sample chamber;
   c) collecting a fluoresced light energy emerging from the sample chamber;
   d) separating the fluoresced light energy from a residual excitation light energy along the light path, with a beam splitter, and sensing the fluoresced light at a detector that is configured to generate a detector output signal according to the detected fluoresced light energy;
   e) amplifying and digitizing the detector output signal to generate digital data;
   f) transmitting the digital data from within the host organism to a receiver that is external to the host organism;
   g) storing the transmitted digital data in a memory that is in signal communication with the receiver and is external to the host organism; and
   h) at a time interval(s), repeating steps (a)-(g), while varying the illumination intensity and/or excitation wavelength of the excitation light energy to reduce noise levels in the detector output signal.

19. The method of claim 18 wherein transmitting the digital data comprises transmitting wireless data.

20. The method of claim 18 wherein maintaining fluid communication comprises retaining the live cells using a permeable membrane.

21. The method of claim 18 wherein the steps of directing excitation light energy and collecting fluoresced light energy comprise conveying light through a common window.

22. The method of claim 18 further including shielding the sample chamber from residual ambient light.

* * * * *